United States Patent
Ratnakar

(10) Patent No.: US 7,269,476 B2
(45) Date of Patent: Sep. 11, 2007

(54) SMART MEDICINE CONTAINER

(76) Inventor: Nitesh Ratnakar, 8600 S. Liberty La., #2410, Oak Creek, WI (US) 53154

( * ) Notice: Subject to any disclaimer, the term of this patent is extended or adjusted under 35 U.S.C. 154(b) by 0 days.

(21) Appl. No.: 10/905,032

(22) Filed: Dec. 11, 2004

(65) Prior Publication Data

US 2006/0124655 A1 Jun. 15, 2006

(51) Int. Cl.
*G06F 17/00* (2006.01)
*B65H 3/36* (2006.01)

(52) U.S. Cl. .............. 700/236; 700/237; 221/253; 221/254; 221/218

(58) Field of Classification Search ............ 221/253, 221/259, 217, 218, 254; 700/236; 235/132 A, 235/98 C; 702/46, 128; 222/46, 415; 198/461.2, 198/444; 377/50
See application file for complete search history.

(56) References Cited

U.S. PATENT DOCUMENTS

| | | | |
|---|---|---|---|
| 3,900,718 A * | 8/1975 | Seward | ........................ 702/128 |
| 4,405,045 A | 9/1983 | Villa-Real | |
| 4,504,153 A | 3/1985 | Schollmeyer et al. | |
| 4,573,606 A | 3/1986 | Lewis et al. | |
| 4,674,651 A | 6/1987 | Scidmore et al. | |
| 4,753,189 A | 6/1988 | Mastman et al. | |
| 4,763,810 A | 8/1988 | Christiansen | |
| 4,798,309 A | 1/1989 | Stone et al. | |
| 4,838,453 A | 6/1989 | Luckstead | |
| 4,911,327 A | 3/1990 | Sheperd et al. | |
| 4,915,256 A | 4/1990 | Tump | |
| 5,044,516 A | 9/1991 | Hoar | |
| 5,216,975 A | 6/1993 | Bartholomew | |
| 5,239,491 A | 8/1993 | Mucciacciaro | |
| 5,279,422 A | 1/1994 | Adams | |
| 5,412,372 A | 5/1995 | Parkhurst et al. | |
| 5,462,198 A * | 10/1995 | Schwimmer | ................ 221/130 |
| 5,473,703 A | 12/1995 | Smith | |
| 5,495,961 A | 3/1996 | Maestre | |
| 5,751,661 A | 5/1998 | Walters | |
| 5,752,235 A | 5/1998 | Kehr et al. | |
| 5,768,327 A * | 6/1998 | Pinto et al. | ................... 377/11 |
| 5,812,064 A | 9/1998 | Barbour | |

(Continued)

OTHER PUBLICATIONS

United States Statutory Invention Registration No. H1782, Published Feb. 2, 1999, Inventor: Wicks et al.

*Primary Examiner*—Gene O. Crawford
*Assistant Examiner*—Timothy Waggoner
(74) *Attorney, Agent, or Firm*—Boyle Fredrickson S.C.

(57) ABSTRACT

A medicine dispensing system is provided that comprises of a medicine container with an inbuilt pill dispensing assembly which automatically dispenses a prescribed dose of medicine at prescribed times. It alerts the patient when a dose of medicine has been dispensed. The alert signal is a local audio or visual alarm or a remote reminder by phone, wireless network or internet. A modem and communication ports are provided which enable the said medicine container to communicate with remote parties like health care professionals and medical devices such as glucose meter. This feature allows remote medicine management, disease management and health education. An internal microprocessor and a memory chip control and execute electronic functions of the said medicine container. Sensors are provided to detect whether a dose has been dispensed and whether it is consumed. The said medicine container is able to record, analyze and report patient's compliance with a medicine regimen.

26 Claims, 10 Drawing Sheets

U.S. PATENT DOCUMENTS

| | | | |
|---|---|---|---|
| 5,835,455 A | 11/1998 | Hanson et al. | |
| 5,860,563 A | 1/1999 | Guerra et al. | |
| 5,884,806 A * | 3/1999 | Boyer et al. | 700/236 |
| 5,915,589 A | 6/1999 | Lim | |
| 5,975,010 A | 11/1999 | Marshall | |
| 5,979,698 A | 11/1999 | Deal | |
| 6,003,467 A | 12/1999 | Shelton-Ferrell et al. | |
| 6,032,609 A | 3/2000 | Luoma | |
| 6,085,752 A | 7/2000 | Kehr et al. | |
| 6,294,999 B1 | 9/2001 | Yarin et al. | |
| 6,302,295 B1 | 10/2001 | Weisman | |
| 6,314,384 B1 | 11/2001 | Goetz | |
| 6,380,858 B1 | 4/2002 | Yarin et al. | |
| 6,471,087 B1 * | 10/2002 | Shusterman | 600/300 |
| 6,510,962 B1 | 1/2003 | Lim | |
| 6,535,637 B1 | 3/2003 | Wootton et al. | |
| 6,561,377 B1 | 5/2003 | Pearson et al. | |
| 6,574,166 B2 | 6/2003 | Niemiec | |
| 6,604,650 B2 | 8/2003 | Sagar | |
| 6,733,095 B1 | 5/2004 | Rieb | |
| 6,789,497 B1 | 9/2004 | Aiken | |
| 2001/0009398 A1 | 7/2001 | Sekura et al. | |
| 2002/0070227 A1 | 6/2002 | Ferruccio | |
| 2002/0093427 A1 | 7/2002 | Roth et al. | |
| 2002/0093429 A1 | 7/2002 | Matsushita et al. | |
| 2002/0169635 A1 | 11/2002 | Shillingburg | |
| 2003/0043026 A1 | 3/2003 | Noble et al. | |
| 2003/0086338 A1 | 5/2003 | Sastry et al. | |
| 2003/0183642 A1 | 10/2003 | Kempker, Sr. | |
| 2004/0035878 A1 | 2/2004 | Aylward | |
| 2004/0045978 A1 | 3/2004 | Peng et al. | |
| 2004/0081023 A1 | 4/2004 | Ho | |

* cited by examiner

SMART MEDICINE CONTAINER

FIELD OF INVENTION

The present invention relates to medicine containers, more specifically to a medicine container with an inbuilt pill dispensing assembly that automatically dispenses a prescribed dose of medicine at prescribed times. According to another aspect, the present invention relates to medicine containers that communicate with remote parties like health care professionals and ancillary medical devices like a glucose meter. According to yet another aspect, the present invention relates to medicine containers that monitor and report patient compliance with a medicine regimen.

BACKGROUND AND PRIOR ART

The advances in medicine are enhancing the quality and longevity of human lives. Ailments, for which there were no effective treatments before, are now effectively treated by one or more drugs. In many cases, patients have to remember to take a dose of medicine at prescribed times. A number of ailments require treatment with one or more combination of medicines. With most medicines (e.g., pills, syrups), doses have to be taken at specific intervals (every six hours) or at certain times of the day (morning, afternoon, evening, before bed time etc). A patient may have difficulty remembering to take medicine at recommended times. Sometimes, patients have difficulty remembering that they have already taken a dose. Some patients have difficulty remembering the recommended dose of medicine to be taken, especially if a medicine dose requires more than one pill of the same medicine. In a multiple drug regimen, such a scenario is even more convoluted and may pose grave consequences to the patient. This is especially true for patients with inadequate skills or knowledge to follow a medicine regimen like elderly, disabled and cognitively impaired and patients with psychiatric disorders (Levy R L et al, American Journal of Gastroenterology 1999; 94:1733-1742 & Nigro J, Journal of Clinical Gastroenterology 2001; 32:66-82). This segment of the population is the most vulnerable as their medicine regimen usually comprises of multiple medicines, each with a different schedule and a different set of instructions. In addition, eyesight fade with age and reading labels of medicine containers can present a problem. Even young and alert patients are sometimes overwhelmed by life, work, family and other responsibilities and forget to take their medicines. This is especially apparent with temporary treatments, such as antibiotics, where the medicine is only taken for a short period of time. In this case, patients are unable to generate a routine based around taking the medicine. The end result of the above situations is that the amount of medicine taken is either too low to affect the course of the ailment, or is too high and causes overdose reactions.

There are many studies that show that management of chronic diseases is unsatisfactory in spite of the great advances in medicine. Factors that have been implicated are 1) poor compliance with medicine regimen because patients forget to take their medicines 2) frequent need to go the pharmacist for refills and education 3) need for frequent visit to the health care professional's office to monitor the treatment response and to make any required changes in medicine regimen 4) lack of adequate health education and inadequate reinforcement thereof 5) under or over dosing of medicine 6) altered dosing regimen 7) incorrect administration of medicine (Kane S et al, Advanced Therapy for Inflammatory Bowel Disease; 2002:9-11). Even more worrisome is the practice that patients do not inform physicians of their non compliance with medicine regimen. Physicians, in such a case, conclude that patient's condition is not responding to the current medicine regimen and make changes in medicine dose, add or substitute another medicine. This results in unnecessary changes in patient's medicine regimen which can be detrimental to the health of the patient. This practice also increases health care cost.

Medicines including pills, capsules, tablets, caplets and the like have traditionally been packaged in bottles or other such containers capped with a variety of closure devices. The caps or closures for these containers have taken a variety of forms and, more recently, have included a key system, depress-and-turn system, or the like, designed to prevent small children from gaining access to the contents. These medicine containers do not have features to assist patients remember to take their medicines or to record their compliance with a medicine regimen. There are many prior art attempts to address problems of this nature which generally incorporate some type of a time, date or dosage indicating device on the cap or other part of the container which involves a moveable pointer or other such device designed to be indicative of the status of medicine administration. These devices generally involve the relative motion of a pointer, plate or other indicator relative to a dial which is moved each time the medicine container is used to indicate the fact that the medicine has been taken and/or the time when the next dose is due.

Systems including a pointer and dial indicator on the container cap are illustrated. In U.S. Pat. No. 5,279,422, Adams disclosed a device suitable as a closure cap for a medicine container. The device has indicia circumferentially marked on the upper surface of the device representing the time for next taking the medicine in the container. An arm rotatably and pivotably mounted in the center of the device is set to point at the time for next taking the medicine. The arm is releasably retained in position by cooperating pegs and indentations on the upper surface of the device and the underside of the rotatable arm. In U.S. Pat. No. 5,216,975, Bartholomew disclosed a combination medicine container cap and indicator device adapted to function as the closure or cover for a medicine container or container. The device includes an indicator providing a visual indication for the user that a pill has been or should be removed from the bottle for consumption. While these approaches are viable as long as they are properly used, the indicating position is easily altered and presents no reliable permanent record.

Various other devices include mechanical advancing systems that coordinate with the operation of the bottle cap. In U.S. Pat. No. 4,753,189, Mastman et al, disclosed a medicine bottle unit having a closure for indicating dosage and other information, which changes automatically as the closure is rotated on the bottle of the unit. The closure includes an outer cap and an inner member within the cap. The cap and inner member have co-operable indicia thereon. The inner member moves with the cap as the cap is rotated in one direction on the bottle. However, the cap moves relative to the bottle and the inner member when the cap is rotated in the opposite direction on the bottle, thus assuring a change in the information represented by the indicia on the cap and the indicator on the inner member, or by indicia on the inner member visible through a hole in the cap. Several embodiments of medicine bottle unit are disclosed. In U.S. Pat. No. 5,975,010, Marshall disclosed indicators and methods of indicating which are intended primarily for use with medicine containers. The devices typically indicate the number of doses of medicine ingested or remaining to be taken by a patient during a particular period. These devices additionally provide tactile assistance to patients in appropriately repositioning the indicator arms and, when used correctly, may reduce the possibility of patient overdose by restricting improper attempts to advance the indicator arm. In U.S. Pat. No. 4,405,045, Villa-Real disclosed a color-coded, two-component medicament container comprising a cap means with variously pre-set structural interval spacing between each pair of preformed window system to differentiate a fixed three-hour time interval cap from a four-hour interval cap, a six-hour time interval cap, an 8-hour time interval cap and from a unitary pre-formed window for a 12 or 24-hour time interval cap; each kind of cap to be specifically used according to the prescribed frequency of drug administration such as every 3-hour frequency, every 4-hour frequency, every 6-hour frequency, every 8-hour frequency and every 12 or 24-hour frequency, respectively, as coordinated in a snug-fitting but csafety lock wisely rotatable engagement with a complementarily shaped cylindrical medicament container having csafety lock-like numeral indicia ranging from 1 to 12 and equidistantly arranged as in a csafety lock there around the supper circumferential exterior wall of the said medicament container is disclosed.

Both, use of the dial or pointer devices and operation of container cap, require manual dexterity and intact cognition. Moreover, with these devices, patients have to learn complex instruction each time a change is made in medicine dose or frequency. Both these are problematic in elderly, disabled or in patients with cognitive impairment.

The need for a device that automatically dispenses the proper pill(s) in the proper amount(s) at the proper time(s) each day and alerts the user to take the dispensed pill(s) is evident by the numerous devices described in the prior art. In U.S. Pat. No. 4,915,256, Tump disclosed a dispensing assembly for dispensing a series of different pills over a prescribed period. The dispensing assembly is provided with an indicator that is adjustable to preset the start of the pill regiment on whatever day desired. The pill package and dispensing assembly are constructed and arranged so that after the indicator has been preset, the pill package can be fixedly positioned in the dispensing assembly with the first pill of the regimen in position to be taken by the user on the first pre selected day. In U.S. Pat. No. 5,915,589, Lim has disclosed a device that can be loaded with appropriate pills and programmed to automatically dispense the proper amount(s) and proper type(s) of pill(s) at the proper time(s) each day. The device also includes a system for alerting the pill taker that pills have been dispensed and need to be taken, a system for providing voice messages to coach the pill taker to use the device and consume the pills, a system for alerting an off-site caregiver when the pill taker has not responded as required or when there is a problem with the operation of the device, and a system for an efficient and accurate loading of pills into the device.

In U.S. Pat. No. 4,573,606 Lewis et al., in U.S. Pat. No. 4,674,651 Scidmore et al., in U.S. Pat. No. 4,838,453 Luckstead and in U.S. Pat. No. 5,044,516 Hoar have described an automatic pill dispensing assembly that has pill storage regulating wheels that are rotated constantly by electric safety lock motors. The constantly rotating pill storage regulating wheel of these devices successively moves each pill storage compartment of the regulating wheel into a temporary alignment with a pill discharge outlet at a cyclical and fixed time interval. When a pill storage compartment is in alignment with the pill discharge outlet, any pill stored in the compartment will fall by gravity through the outlet into a pill receptacle. Automatic pill dispensing assemblies that do not employ rotating wheels are also known. For example, U.S. Pat. No. 4,763,810 to Christiansen shows a device that uses a series of pill storage compartments that are arrayed in a checkerboard fashion and U.S. Pat. No. 4,798,309 to Stone et al shows a device that uses a series of pill storage compartments that are spirally arranged on an elongate cylinder. Although these examples seem to be different, the basic operating principle of all these dispensing assemblies, are nonetheless similar.

However, there are problems with the devices described in the prior art. These devices entail loading of individual pill storage compartments by the pharmacist. This is a time consuming and manpower intensive process that makes these devices costly and inefficient. None of these devices provide the ease and cost effectiveness of the present day throwaway plastic medicine containers where a bulk supply of medicaments can be dispensed at one time.

There have been many prior art attempts to incorporate a device into the medicine container that is able to record the opening and closures of the caps of the medicine containers. These prior arts have attempted to use the operation of the closure of medicine container as a surrogate marker for compliance. In U.S. Pat. No. 6,604,650 Sagar has proposed a medicine-dispensing system that has a medicine reminder to assist the patient in following a drug regimen. In an example embodiment, a medicine reminder comprises a timer programmable to a predetermined interval. A user-alert is responsive to the timer, reminding the user to take a dose of medicine at the predetermined interval. A sensor detects whether the medicine container cap has been opened and a dose-indication informs the user of the time since the last dose. The dose indication further informs the user as to whether to take a next medicine dose. The time of the last dose is determined by the timer receiving a signal from the sensor. A communications interface enables programming of a parameter associated with administering a medicine.

There are major disadvantages to the inventions that rely on medicine container cap removal as a measure of compliance. Medicine containers with cap allow access to the bulk medicine supply during each dispensing event. Once the device recognizes the removal of the cap, any number of doses may be removed from the bottle without proper recognition, thus seriously compromising the device's ability to properly record compliance. Even more troublesome is the possibility that the cap device might not be reinstalled on the bottle; if not, the subsequent removal of medicines from the bottle go unmonitored.

In addition, the devices described in prior inventions share some common drawbacks that include: 1) none of the prior art devices have the ability to automatically count and dispense a prescribed quantity of medicine at prescribed times from a bulk supply within the medicine container. 2) These devices do not provide any protection against abuse of prescription medicines. Once the closure is opened any number of doses can be removed. This is of particular concern with medicines that have a high abuse potential such as morphine. 3) The prior art devices do not provide any protection against the consumption of medicines that have expired. Medicines that are beyond their expiry date are associated with significant life threatening side effects. 4) They do not provide security features to prevent use by a person other than the intended patient. 5) Devices proposed by the prior inventions do not allow for remote medicine management. Whenever a change is made to a medicine regimen, a new prescription has to be filled and the medicine container has to be taken to the pharmacist for a change of label. The patient has to learn new information regarding the new dosage regimen. These are major deterrents to continued compliance with pharmacotherapy for chronic medical conditions. 6) Prior art devices do not assist with comprehensive disease management. Adequate disease management requires frequent monitoring of health related parameters to assess the efficacy of medicines. Studies have shown that frequent home based monitoring of health parameters and subsequent prompt adjustment of treatment regimens significantly improves disease outcomes. At the present time, such monitoring, reporting and adjustment of medicine regimen requires intensive participation by patients, including multiple visits to health care professional's office. Prior art devices do not provide a solution to this problem. 7) The devices of prior inventions are cumbersome and expensive to manufacture. None of the prior inventions have provided the necessary reliability and inexpensive implementation to present itself as a viable alternative to today's plastic throwaway medicine containers. The value of additional features suggested by the prior inventions, have not justified the added costs.

Some prior art devices provide limited solution to individual problems faced by patients, health care professionals and pharmacists in ensuring compliance. However none of these devices have provided a comprehensive one stop solution to manage the multiple complex problems that hinder patient's compliance with a medicine regimen. Hence, while "childproof" construction has been mandated, to date there has been no other major addition to the conventional throw away plastic medicine containers.

SUMMARY OF INVENTION

The present invention discloses a next generation medicine container, hereby referred to as "smart medicine container", which improves patient compliance with a medicine regimen and assists with disease management. None of the prior art devices disclose the unique features of the present invention.

The smart medicine container has an accurate and reliable automatic pill dispensing assembly that is built into the container itself. It is capable of automatically dispensing medicines according to the instructions of the prescription. It has an audio and visual alarm that alerts the patients when a medicine dose has been dispensed and ready to be taken. According to another aspect of the invention, the medicine container provides means for recording, analyzing and reporting patient's compliance with a medicine regimen. According to another aspect of the present invention, the medicine container has a modem and communication ports which enable it to communicate with remote parties like health care professionals and medical devices like a glucose meter, blood pressure monitor etc. It can send remote reminders to patients, is able to receive remote instructions from physicians and has means to accordingly change a medicine regimen. In addition, it is able to retrieve information from medical devices and has the means to accordingly modify a medicine regimen. It sends information obtained from medical devices to physicians, who can then remotely change medicine regimen. According to yet another aspect of the invention, the medicine container has an electronic display unit which displays medicine and other health related information. The present invention also provides means for a web based comprehensive medication management solution. According to another aspect of the present invention, the smart medication container provides advanced security features to prevent misuse of prescription medications.

DETAILED DESCRIPTION OF THE PRESENT INVENTION

Figure 1A:
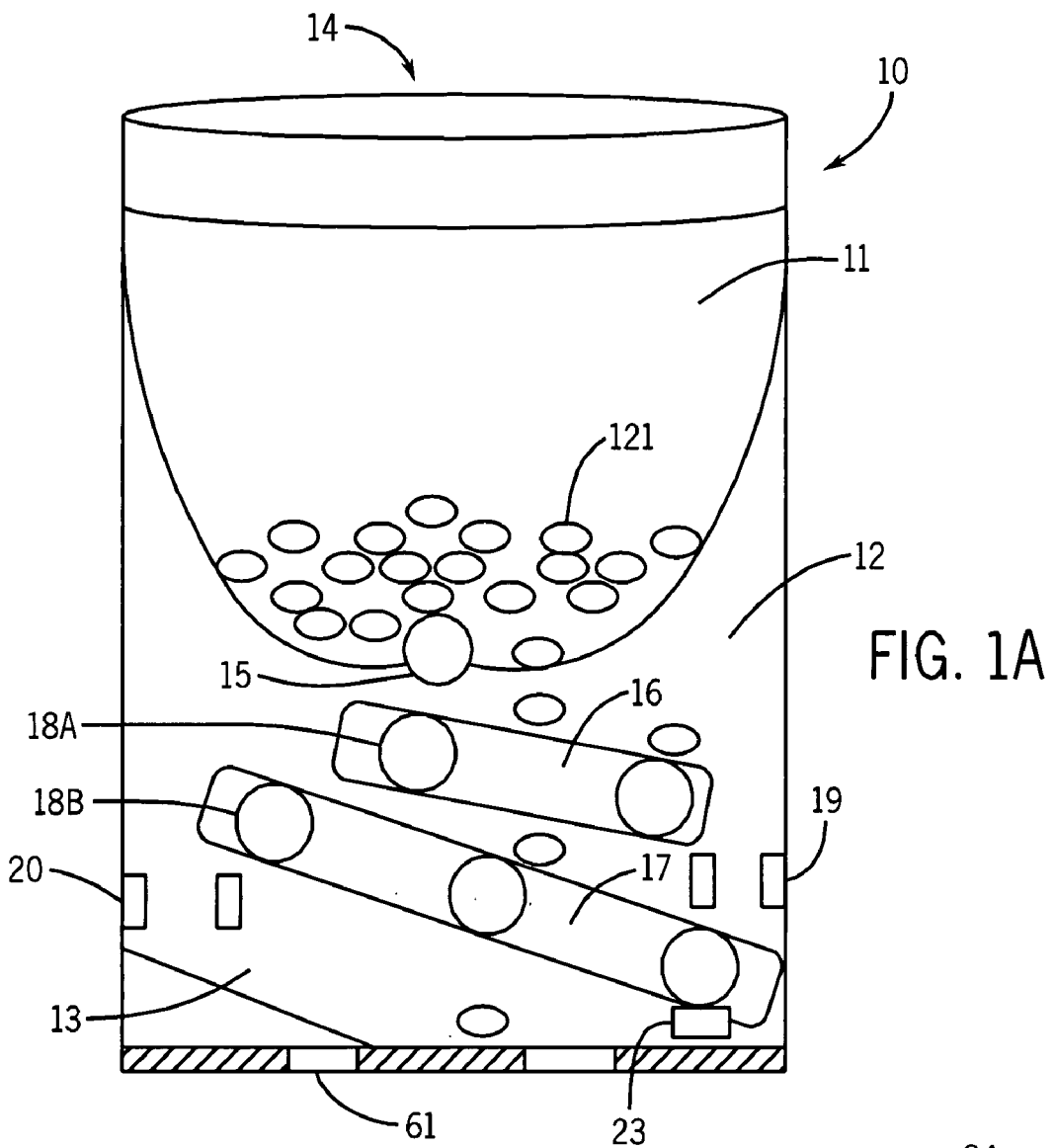
FIG. 1A is a coronal section of the smart medicine container and shows the pill dispensing assembly built into the medication container itself.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out one or several purposes of the present invention. It is important, therefore, that the claims be regarded as including such equivalent constructions insofar as they do not depart from the spirit and scope of the present invention.

Figure 1B:
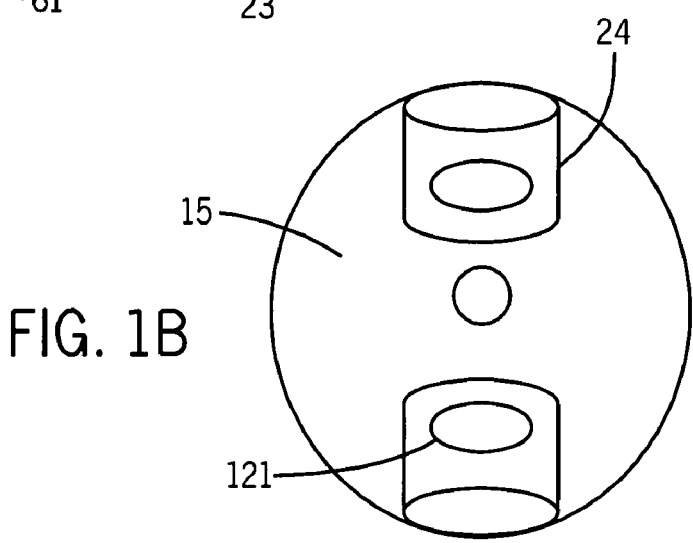
FIG. 1B shows the regulating wheel with two pill receptacles.
Figure 3:
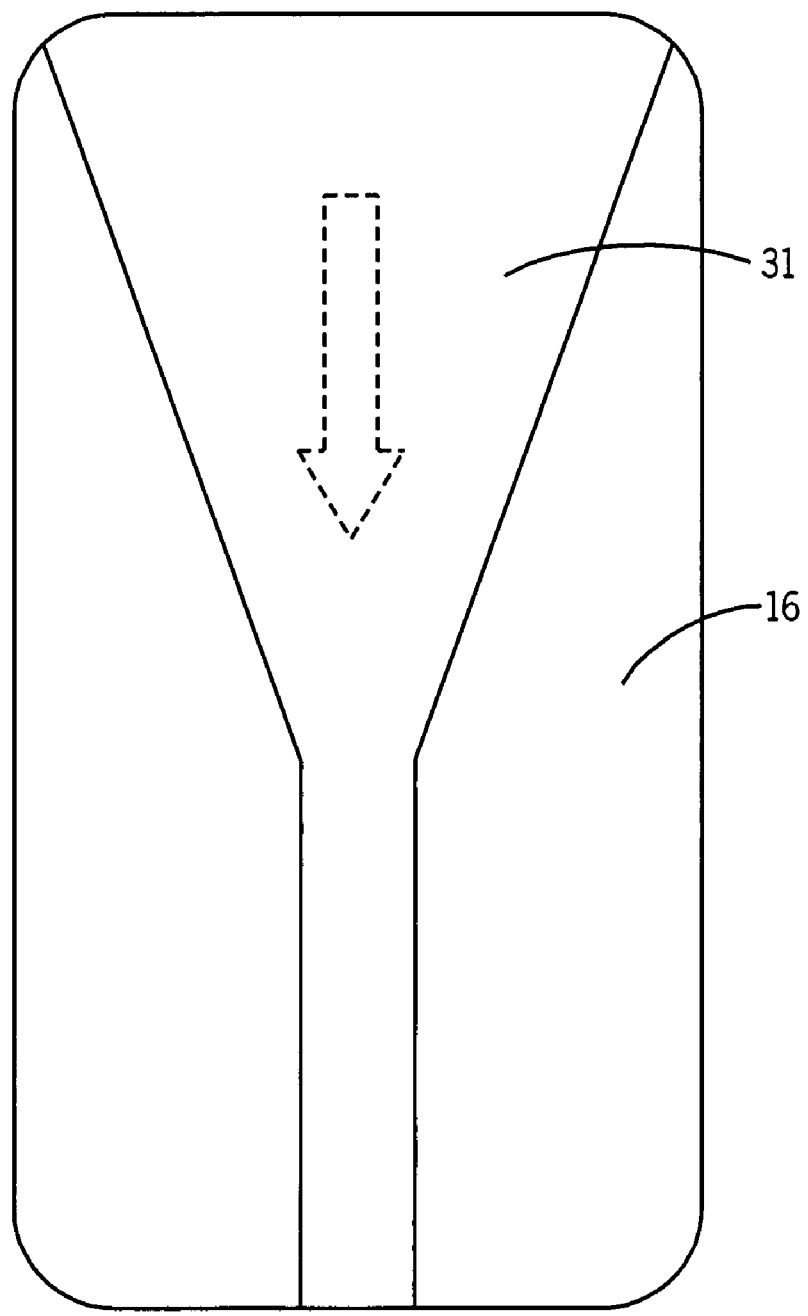
FIG. 3 shows the collecting conveyor belt with a 'Y' shaped pill organizer located above it.

Medicine Container:

As shown in FIG. 1A, the present invention comprises of a smart medicine container (10) that has an inbuilt pill dispensing assembly. The medicine container in the preferred embodiment is elliptical in shape but it may be of any convenient shape and size. It has three compartments—storage compartment (11), counting compartment (12) and dispensing compartment (13) that is stacked on top of one another. The storage compartment (11) is located at the top and is 'U' or 'V' shaped. It has an aperture at the bottom to allow the passage of pills (121) into the counting compartment (12) which is guarded by a regulating wheel (15). The pill dispensing assembly of the present invention has an inbuilt pill counting apparatus that provides the means to automatically dispense a desired quantity of medicine at desired times from a bulk supply within the smart medicine container (10). The pill dispensing assembly comprises of a regulating wheel (15) will two pill receptacles (24), a collecting conveyor belt (16), a dispensing conveyor belt (17), motors to power the conveyor belts and the regulating wheel and a multitude of photoelectric sensors placed along the path of relay of the pills (121). A microprocessor (71) present within the smart medicine container regulates the operation of the entire pill dispensing assembly. The regulating wheel (15) is powered by a motor (not shown) and has two pill receptacles (24) placed at 180 degrees from each other (FIG. 1B). It guards the aperture between the storage and counting compartments. The pill receptacles (24) collect pills (121) when facing the storage compartment (11) and discharge them onto the collecting conveyor belt (16) when facing the counting compartment (12). The regulating wheel (15) provides the means for a controlled and orderly discharge of pills (121) from the storage compartment onto the collecting conveyor belt (16) in the counting compartment (12). The regulating wheel (15) also prevents migration of pills (121) out of the storage compartment (11) when it remains idle. The counting compartment (12) is located in the middle and has a collecting conveyor belt (16) on top, a dispensing conveyor belt (17) below and photoelectric sensors (19&20) that line the path of relay of pills (121) along the conveyor belts. The collecting conveyer belt (16) has a 'Y' shaped pill organizer (31) located above its surface, shown in FIG. 3, which aligns the pills (121) in one column for an orderly discharge onto the dispensing conveyer belt (17). In the preferred embodiment shown in FIG. 1A, the passageway from the collecting conveyor belt (16) to the dispensing conveyer belt (17) has photoelectric sensors (19), but any other suitable sensing instrument can be used. The dispensing conveyor belt (17) collects pills (121) from the collecting conveyor belt (16) and discharges them into the dispensing compartment (13). The dispensing conveyor belt (17) again has a 'Y' shaped pill organizer located above its surface which aligns the pills (121) in one column for an orderly discharge into the dispensing compartment (13). In the preferred embodiment, the passageway from the dispensing conveyer belt (17) to the dispensing compartment (13) has photoelectric sensors (20), but any other suitable sensing instrument may be used. The collecting and the dispensing conveyor belts move on two separate sets of wheels (18A&18B) that are powered by motors (not shown). In the preferred embodiment, the speed of the dispensing conveyor belt (17) is greater than of the collecting conveyor belt (16). The dispensing compartment (13) is located at the bottom and has an outlet door (22) through which pills (121) is dispensed to the patient. The outlet door (22) has a sensor (23) which captures its operation.

Figure 2:
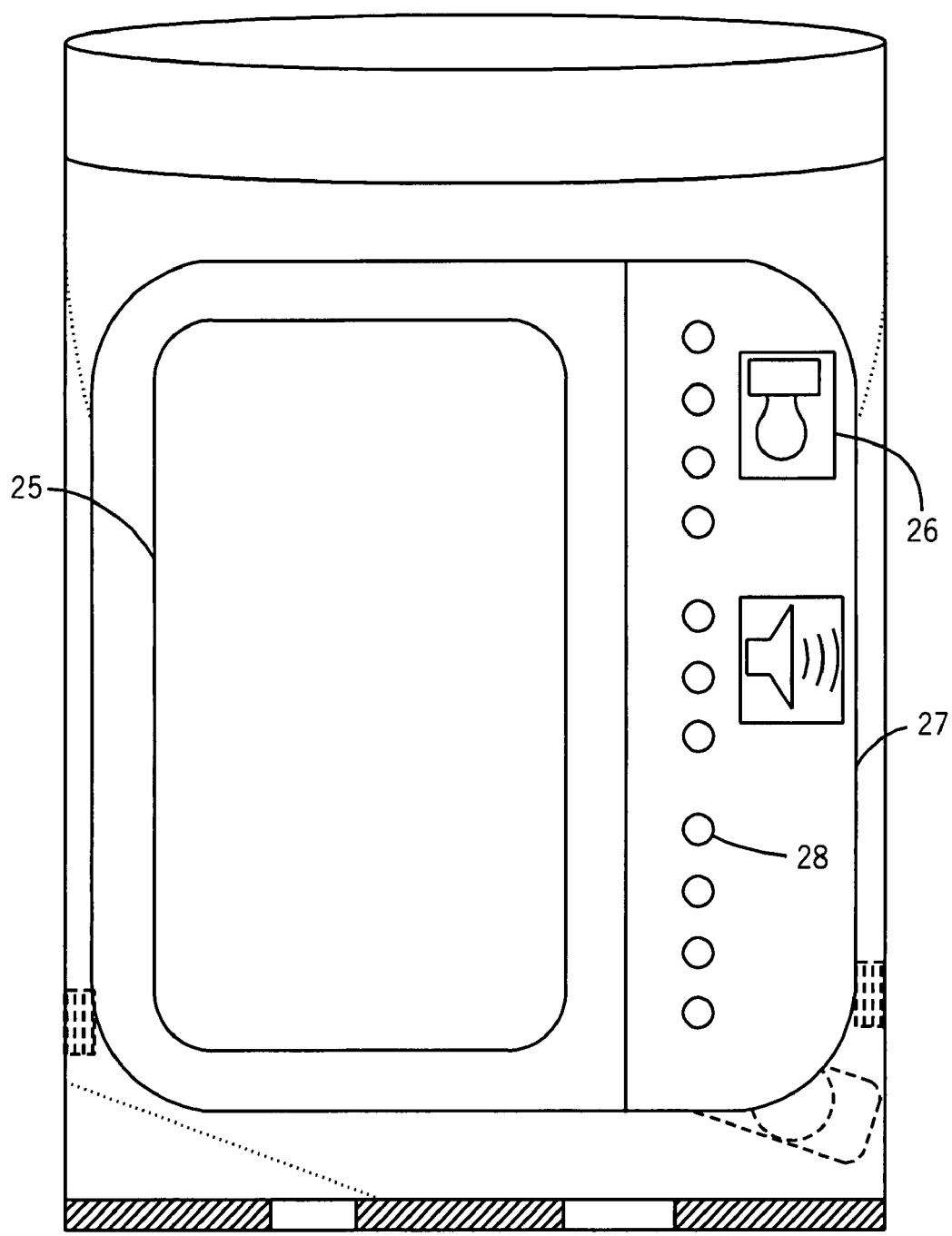
FIG. 2 is a front view of the smart medicine container showing the electronic display unit, audio speakers, visual alarm and a plurality of control switches.

FIG. 2 shows the anterior aspect of the smart medicine container. A plurality of control switches (28) are provided that can be used for multiple purposes, including but not limited to—1) as a keypad for command and data entry 2) to actuate display of compliance data and other information in different formats 3) as a keypad for operation of the universal safety lock (73). An audio speaker (27) and a visual alarm (26) are provided that is activated when a dose of medicine is ready to be taken. FIG. 2 also shows an electronic display unit (25), which in the preferred embodiment is a liquid crystal display (LCD) screen.

Figure 4:
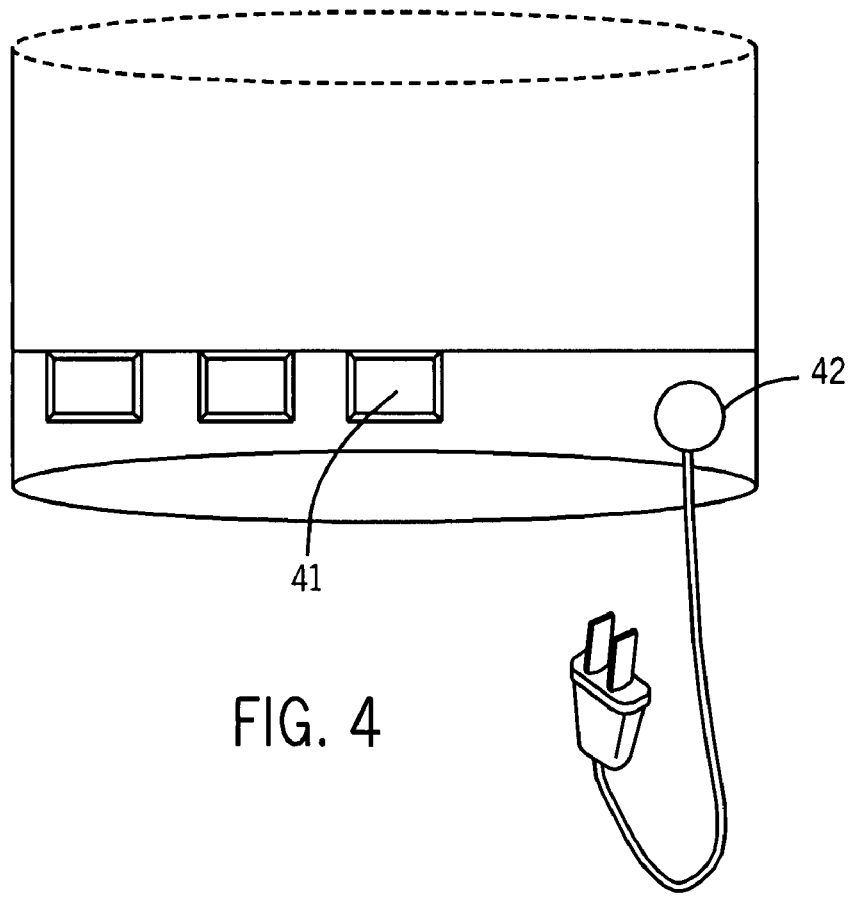
FIG. 4 is a posterior view of the lower part of the smart medicine container showing the communication ports and electrical inlet.
Figure 5:
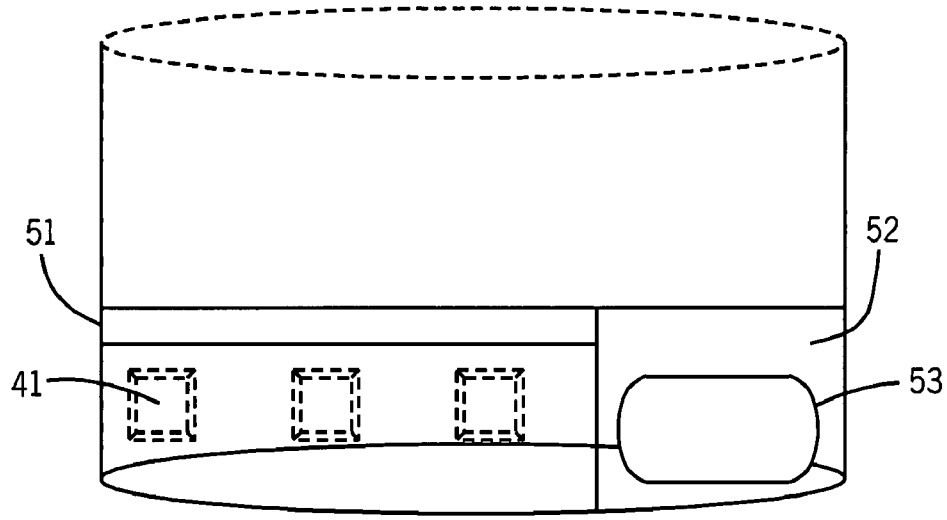
FIG. 5 is a coronal section of the lower part of the smart medicine container showing the modem with wireless transceiver, communication ports and battery compartment with a battery.

FIGS. 4&5 show the posterior and saggital views of the lower part of the smart medicine container respectively. A modem (51) and three communication ports (41) are provided which enable the smart medicine container (10) to send and receive communication from external devices via telephone line, wireless network, internet, LAN or any other communication network. In the preferred embodiment, the modem (51) also contains a wireless two-way transceiver. Alternatively, the wireless transceiver can be present separately. Data can be transferred between the smart medicine container (10) and a computing device such as pharmacy or physician computer using the communication ports (41). A battery compartment (52) containing a battery (53) is provided which powers the smart medicine container. In addition, an electrical inlet (42) is provided which serves as an alternate source of power for the smart medicine container.

Figure 7:
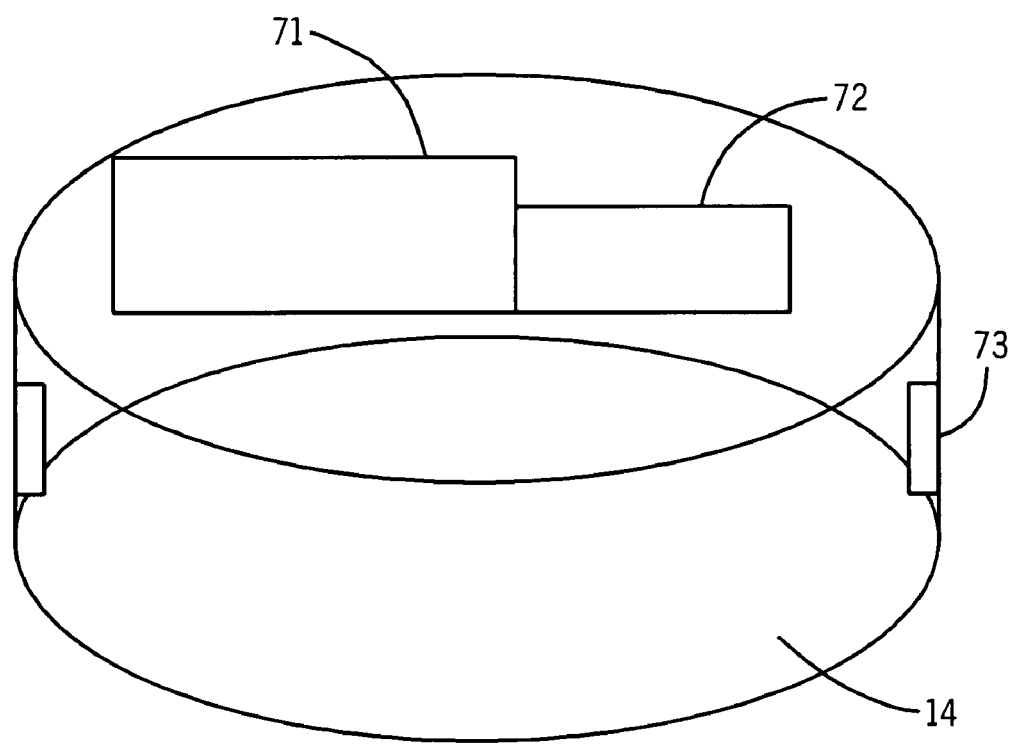
FIG. 7 is a transparent view of the cap of the smart medicine container showing the microprocessor, memory chip and universal safety lock

The smart medicine container (10) is covered on top by a cap (14) shown in FIG. 7. In the preferred embodiment, the cap (14) has a universal safety lock (73) that is operable by a unique combination of numbers that is entered using the control switches (28). Alternatively, the universal safety lock (73) can be coupled with a radio frequency identification (RFID) reader. The universal safety lock (73) in this case is operable when the RFID reader reads an authorized RFID tag. Authorized users having an authorized RFID tag will be able to operate the universal safety lock (73). The safety lock (73) adds a safety feature to the smart medicine container (10) and allows only authorized access to the contents thereof. The smart medicine container (10) has an internal microprocessor (71) and a memory chip (72) located in the cap (14). The electronic apparatus of the smart medicine container (10) is hardwired to the microprocessor (71) and memory chip (72). The microprocessor (71) is programmed to execute various functions of the smart medicine container (10) including, but not limited to, data analysis, operational control of electronic functions and external communication. The memory chip (72) stores operational data, information about the contained medicament and any other relevant information. The smart medicine container (10) has an internal clock with a timer (not shown) which triggers the time sensitive functions of the smart medicine container (10).

Figure 6:
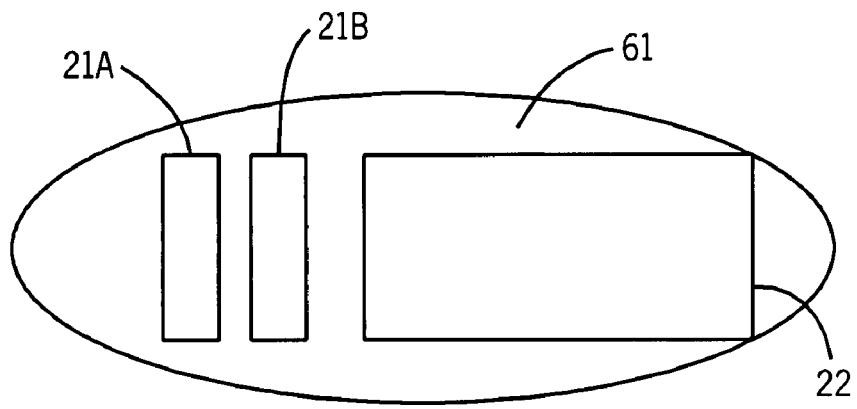
FIG. 6 is a view of the bottom surface of the smart medicine container showing the docking port, electrical port and the outlet door.
Figure 8:
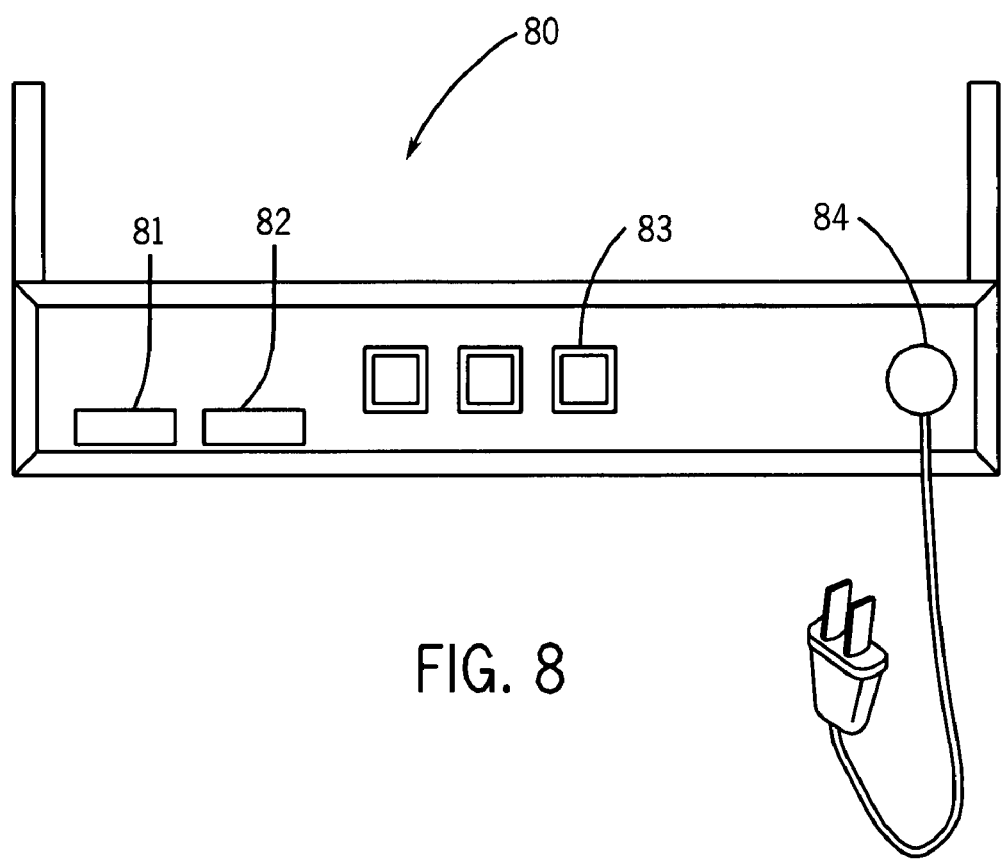
FIG. 8 is a posterior view of the sync cradle showing the docking terminal, electrical terminal, communication ports and electrical inlet.

Now referring to FIG. 6, a docking port (21A) and an electrical port (21B) are provided on the bottom of the smart medicine container (10). It also houses the outlet door (22). FIG. 8 shows a 'sync cradle' (80) with a docking terminal (81) and an electrical terminal (82) that are adapted for operative engagement with the docking port (21A) and electrical port (21B) of the smart medicine container. Three communication ports (83) are also provided. The docking port (21A) along with the docking terminal (81) and communication ports (83) enable the smart medicine container (10), while it is sits in the sync cradle, to communicate with external communication devices. An electrical inlet (84) is provided which, along with electrical terminal (82) and electrical port (21B) powers the smart medicine container during the time it sits in the sync cradle (80). The sync cradle (80) is provided as an optional gadget that would help reduce the size and weight of the smart medicine container (10) and improve its portability. It also provides a more convenient way to transfer data between the smart medicine container (10) and other computing devices such as a pharmacy or physician computer.

Operation:

According to one aspect of the present invention, a smart medicine container (10) is connected to the pharmacy computer using the communication ports (41). Alternatively, it can be connected to the pharmacy computer by placing it in the sync cradle (80) that is connected to the pharmacy computer. The smart medicine container (10) can also communicate with the pharmacy computer wirelessly using the wireless transceiver. Pharmacist enters the medicine data including medicine name, strength, dose, frequency, physician information, authorized refills, expiration date and other relevant information. The pharmacist also enters the time the first dose is to be dispensed and time from which automatic dispensation will commence. The pharmacist can have pre programmed time regimen for various administration schedules. For example QID regimen (four times a day) may mean that the medicine is to be taken at 8 AM, 12 PM, 4 PM and 8 PM everyday or it may mean that the medicine is to be taken at 7 AM, 11 AM, 3 PM and 7 PM everyday. Pharmacies can have their own time regimen, there can be a universal time regimen or there can be a time regimen customized according to patient's preference and habits. Additional data, like patient's allergies, drug to drug and drug to food interactions, medicine adverse/side effect can be entered. This information is stored in the memory chip (72) and displayed on the electronic display unit (25) of the smart medicine container (10). In effect, the electronic display unit (25) replaces the paper label of conventional medicine containers. However, it is to be appreciated that the electronic display unit (25) provides a more dynamic, comprehensive and interactive platform to access information about the contained medicine. The microprocessor (71) uses the entered information to regulate the dispensation of medicine and to perform other functions of the smart medicine container (10). It also uses this information to analyze and report patient's compliance with a medicine regimen. Using this system, the pharmacist has no additional responsibility besides his/her normal customary responsibility to enter pertinent medicine information in the pharmacy computer system, which then automatically programs the smart medicine container (10) with the same information.

Figure 9:
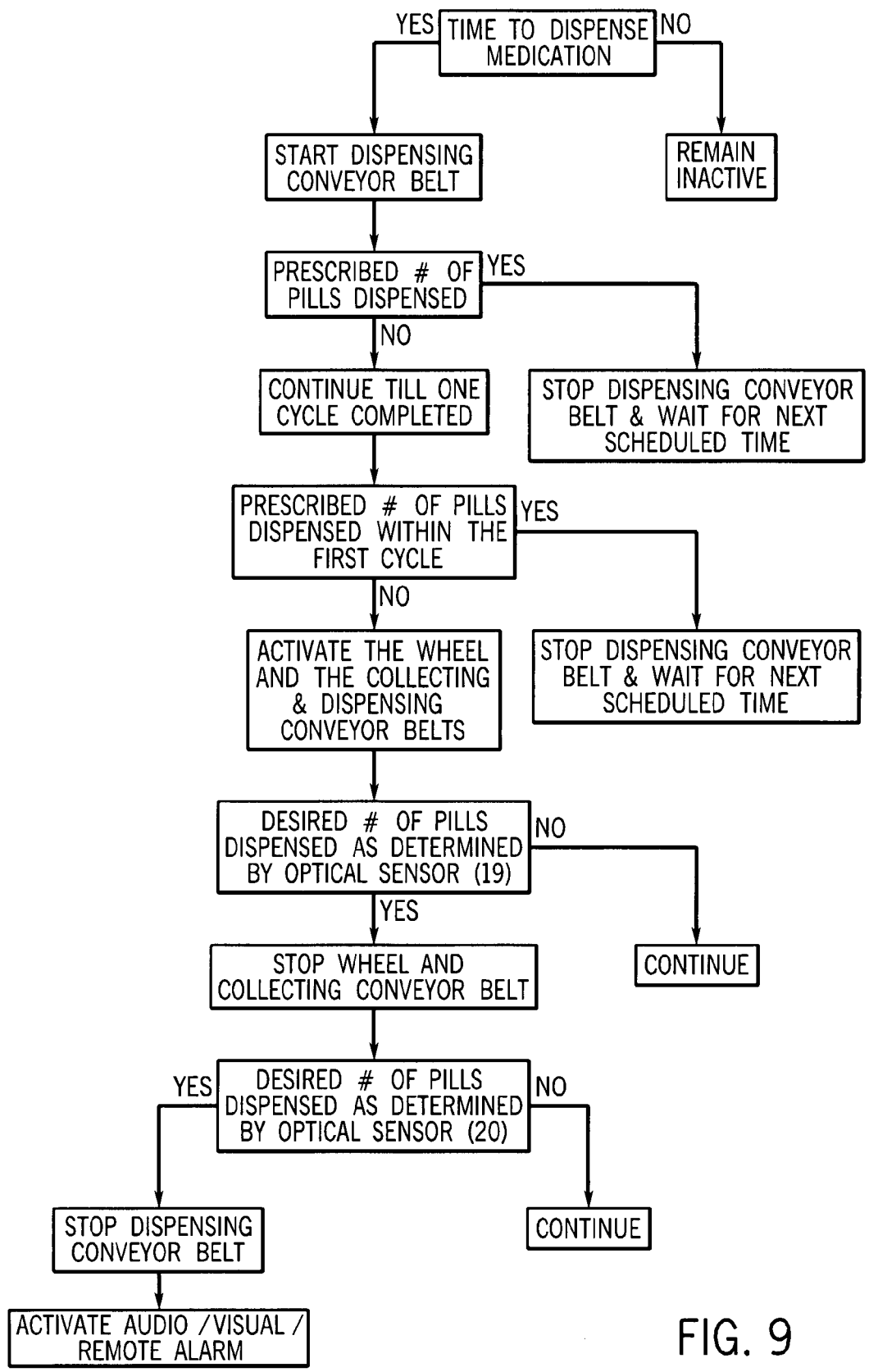
FIG. 9 shows an algorithm of the dispensation cycle of the smart medicine container.

FIG. 9 shows an algorithm that guides the pill dispensing assembly of the smart medicine container (10). Once the predetermined time to dispense medicine arrives, the dispensing conveyor belt (17) is activated. This ensures that any remaining pill on the dispensing conveyor belt (17) from previous cycle is dispensed before a fresh batch is released from the storage compartment (11). The dispensing conveyor belt (17) stops if the desired number of pills (121) is dispensed before completion of one cycle. If the desired number of pills (121) is not dispensed within the first cycle, the remainder of the pill dispensing assembly comprising of the regulating wheel (15) and collecting conveyor belt (16) is activated. The pill receptacles (24) of the regulating wheel (15) collect pills (121) from the storage compartment (11) and dispense them onto a moving collecting conveyor belt (16). The speed of the collecting conveyor belt (16) is greater than the rotational speed of the regulating wheel (15), which amplifies the pill separation provided by the regulating wheel (15). As the pills (121) fall off from the collecting conveyor belt (16) they are counted by photoelectric sensors (19), which relay this data to the microprocessor (71) and memory chip (72). Once the microprocessor (71) senses that desired number of pills (121) have been dispensed, it stops the regulating wheel (15) and the collecting conveyor belt (16). The collecting conveyor (16) transfers the pills (121) onto a moving dispensing conveyor belt (17). The dispensing conveyor belt (17) moves at a greater speed than the collecting conveyor belt which further amplifies the pill separation achieved so far. The dispensing conveyor belt (17) transfers the pills (121) into the dispensing compartment (13). The photoelectric sensors (20) count the pills (121) as they fall from the dispensing conveyor belt (17) into the dispensing compartment (13) and relay this data to the microprocessor (71) and memory chip (72). The dispensing conveyor belt (17) stops once the microprocessor (71) signals that prescribed quantity of pills (121) have been dispensed into the dispensing compartment (13). In effect, the entire pill dispensing assembly of the smart medicine container is inactivated at this time.

The time when a medicine dose is dispensed into the dispensing compartment (13) is recorded as the 'dispensation time' and serves as a measure of reliability of the smart medicine container (10). The reliability data is relayed to the microprocessor (71) and memory chip (72) and can be viewed by an authorized user on the electronic display unit (25) or it can be downloaded to a computer and viewed. The reliability data is also relayed to and stored in a central server and can be accessed by authorized users. The smart medicine container (10) gives an audio and/visual alarm (26) to alert the patient that a medicine dose is due. In addition, after a reasonable wait time after the actual due time, the smart medicine container sends a remote reminder to patient or caregiver by phone, fax, pager, cellular phone, internet or any other communication device preferred by the patient. The patient can turn off the alarm using a control switch (28). The alarm feature of the smart medicine container can also be turned off for a period of time using a control switch (28). This is useful when patients may not want to be disturbed by the alarm such as when they are asleep.

Once a medicine dose is dispensed, the outlet door (22) is unlocked. The patient can open the door and can take his/her medicine. The time of opening of the outlet door (22) is recorded as 'consumption time ' by the sensor (23) and is useful in determining patient compliance with a medicine regimen. This mechanism allows passive recording of compliance data as opposed to active recording wherein patients are required to manually operate a switch to indicate medicine consumption. The compliance data is relayed to the microprocessor (71) and memory chip (72) and can be viewed by an authorized user on the electronic display unit (25) or it can be downloaded to a computer and viewed. The compliance data is also relayed to and stored in a central server and can be accessed by authorized users.

Figure 10:
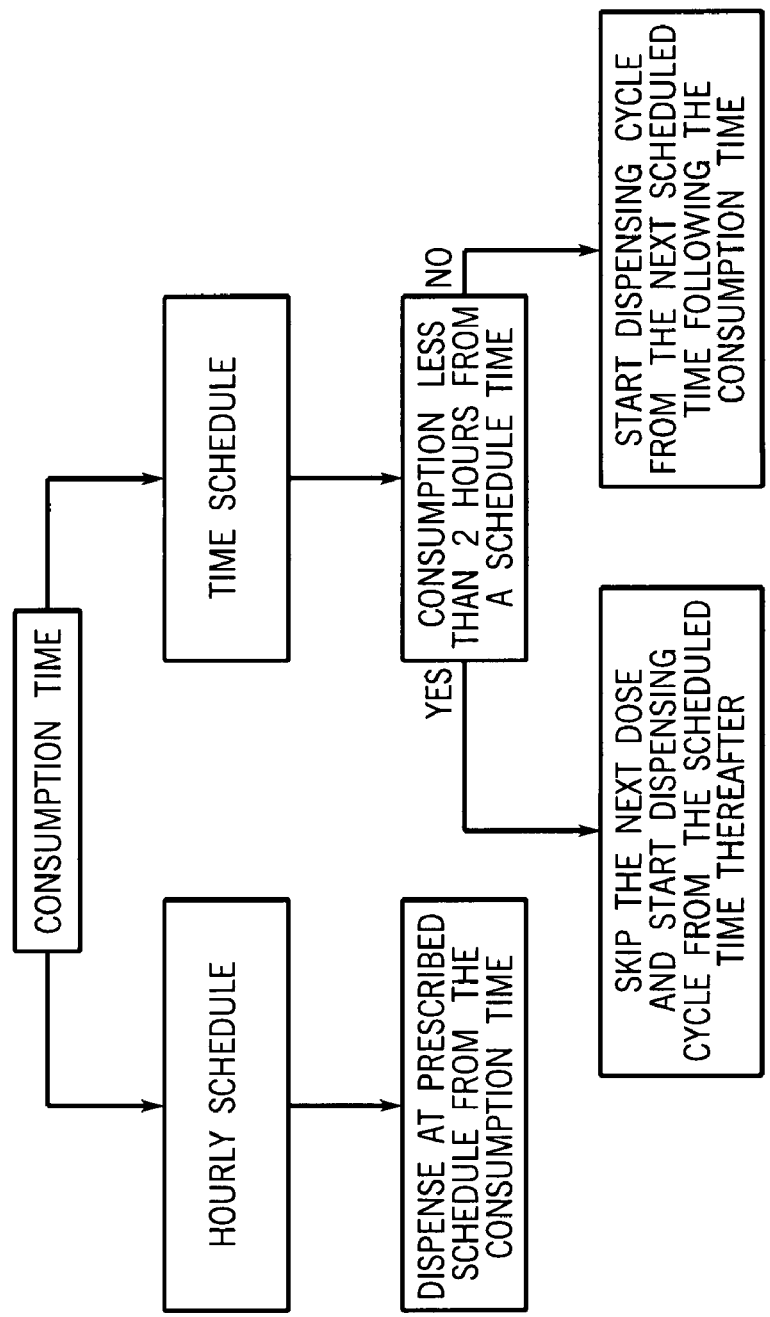
FIG. 10 shows an algorithm of the dispensation cycle of the smart medicine container in relation to the consumption time.

The electronic apparatus of the medicine container remains disabled until the outlet door (22) is opened and then closed. This ensures that another dose of medicine is not dispensed until the previous dose has been consumed. Consumption time is also used as a reference for timing the next dose. As shown in FIG. 10, for medicines that are to be taken at fixed hourly intervals, like every six hours, the next dose is dispensed at the prescribed interval from the consumption time. In case of medicines that are to be taken at certain times of the day, like four times a day, the next cycle starts according to a pre programmed algorithm. In the illustrated example of four times a day, if the consumption time is within 2 hours of a scheduled time, the dose due at that scheduled time is skipped and the dispensing cycle starts from the scheduled time thereafter. Otherwise, the dispensing cycle starts from the scheduled time following the consumption time. This is consistent with the current practice guidelines. Similarly, algorithms for other dosing schedules can be made according to accepted guidelines.

The smart medicine container (10) provides multiple unique safety features 1) the cap (14) has a universal safety lock (73), which in the preferred embodiment is operable by a unique combination of numbers. It allows only authorized access to the contents of the smart medicine container (10). The universal safety lock (73) is connected to the internal clock and can be used for other useful purposes. The universal lock (73) can be programmed to remain open only during the time when a medicine dose is due to be taken. It can also be programmed to automatically lock irreversibly once the contained medicament is past its expiration date. 2) The pill dispensing assembly of the smart medicine container automatically dispenses a prescribed quantity of medicine at desired times. In addition, the pill dispensing assembly remains inactive until the previously dispensed dose has been removed from the medicine container. These features allow access to only one prescribed dose of a medicine at any given time and that too, only when it is time to take a dose. This prevents overdose. In addition the pill dispensing assembly stops dispensing when the contained medicine is past its expiration date which prevents patients from consuming medicines that have expired. 3) The outlet door (22) has a lock that remains locked from the time it is closed until the time a medicine dose is dispensed. This prevents patients from consuming more than prescribed dose of a medicine. In addition, the outlet door locks irreversibly once the medicine in the smart medicine container (10) is past its expiration date which prevents patients from gaining access to an expired medicine. According to another embodiment of the present invention, the outlet door can have a lock that is coupled with a radiofrequency (RFID) reader. Access to the contents of the smart medicine container can be limited to authorized users with a corresponding RFID tag.

According to another aspect of the present invention, the locking apparatus containing a RFID reader can be used for other applications in the pharmaceutical industry. For example, medicine dispensing units used in hospitals can have a lock coupled with a RFID reader. This lock is operable when the RFID reader reads an authorized RFID tag. Authorized RFID tags are given only to authorized users. According to another aspect of the present invention, RFID reader can be coupled with any locking apparatus. The locking apparatus can be made operable when the RFID reader of the locking apparatus reads an authorized RFID tag. It is to be appreciated that this feature of the present invention makes the operation of any such locking apparatus fast, secure and user friendly.

Figure 11:
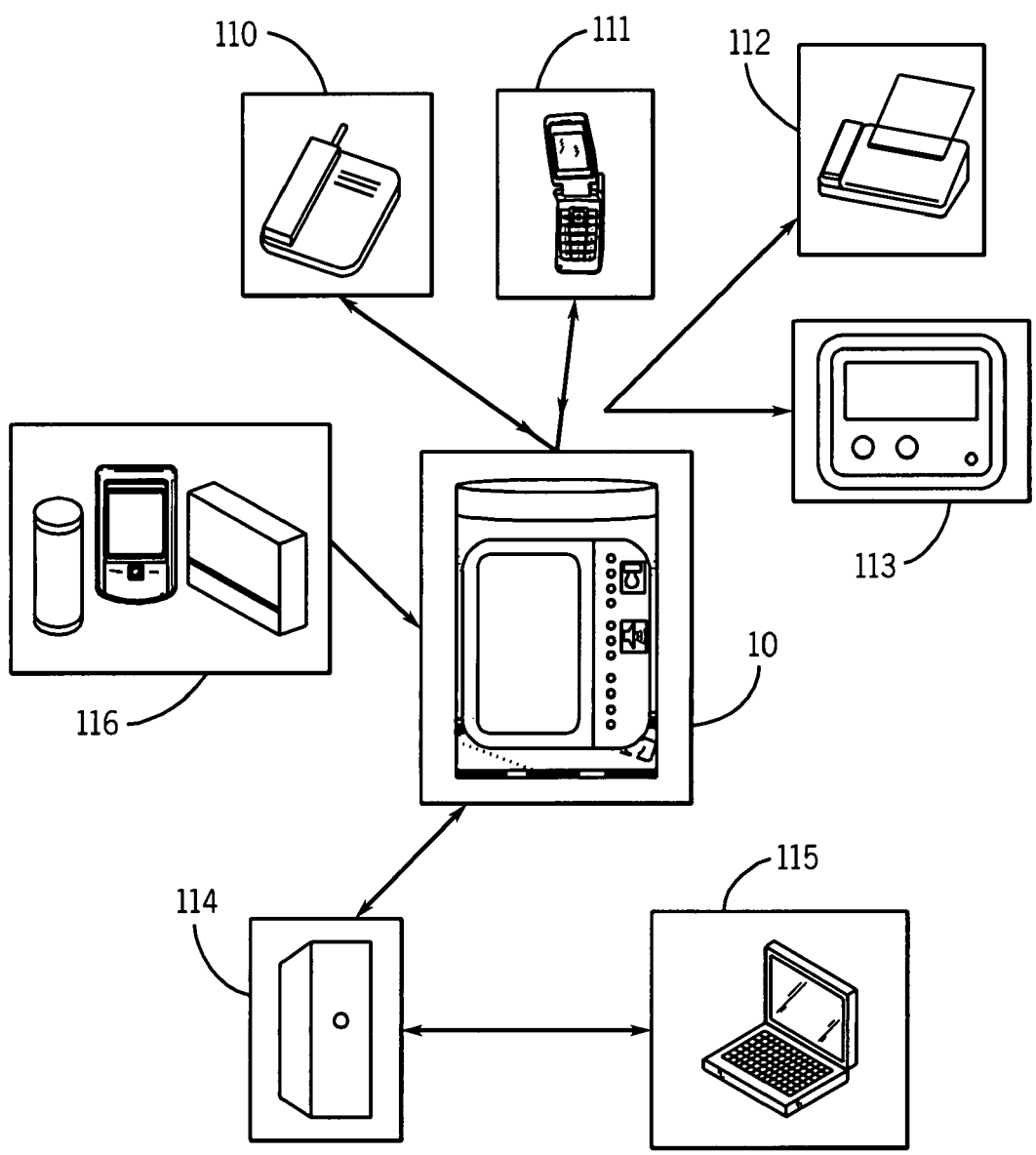
FIG. 11 shows the communication network of the smart medicine container.

According to another aspect of the present invention, a modem (51) and three communication ports (41) are provided in the smart medicine container (10). In the preferred embodiment, the modem (51) also has a two-way wireless transceiver. As shown in FIG. 11, the smart medicine container has means to communicate with external devices including communication devices and medical devices. It can communicate with remote parties like physicians via external communication devices such as phone (110), pager (113), fax (112), cellular phone (111), computer (115), web server (114) and the like using phone line, wireless network, internet, LAN or any other communication network. The smart medicine container (10) is also able to communicate with appropriately configured medical devices such as glucose meter (116), blood pressure monitor, coagulation monitor and the like.

According to another aspect of the present invention, a multitude of smart medicine containers (10) are connected to a central server to form a network. Each smart medicine container (10) has a unique identifier that is readable by the central server. In the preferred embodiment, the unique identifier is a number stored in the memory chip (72). The server has access to data from all smart medicine containers in its network. The server synchronizes with the smart medication containers in its network at frequent intervals to keep the data updated. This has many practical applications—1) The server compiles and stores patient compliance data from the smart medicine containers within its network 2) The server stores the medicine inventory data for individual smart medicine containers within its network 3) The server can serve as a nodal point for communication between the smart medicine container and remote parties like health care providers, enabling them to access patient compliance data and remotely control the functions of the smart medicine container 4) The server stores back up data for the smart medicine containers within its network 5) According to another aspect of the present invention, the server can remotely actuate the functions of the microprocessor (71) and memory chip (72) of the smart medicine container (10) within its network and can thereby, remotely control the functions of the smart medicine container (10). These features have many practical applications some of which are discussed below.

1) Remote Medicine Management: The smart medicine container (10) can send remote reminders to patient or their caregiver when a medicine dose is ready to be taken. The smart medicine container (10) can receive instructions remotely from health care professionals and the pill dispensing assembly can accordingly initiate, modify or discontinue a medicine regimen. It is to be appreciated that patient will have no additional learning to do when these changes are made as the smart medicine container (10) will automatically dispense medicine according to the new instructions. The changes and the new instructions are displayed on the electronic display unit (25) or played in audio using the speakers (27). It is also to be appreciated that patient will not need to go to the health care professional or pharmacist for these changes to be made or to be educated about their new medicine regimen. Similarly, the smart medicine container (10) can send a reminder to the pharmacist when refills are needed. These features are of particular benefit to the elderly as they frequently have trouble learning new information and are commonly unable to drive.

2) Health Education: Health information can be fed into the memory chip (72) at the time a prescription is filled or it can be fed remotely via the modem (51). Patients can view this information on the electronic display unit (25) or it can be played in audio using the speakers (27). The strategic timing of providing health information at the time of consumption of medicines provides a powerful learning tool and will result in improved and lasting retention of the given information. It is also to be appreciated that the smart medicine container provides a dynamic, interactive and flexible platform for health education wherein different messages can be displayed at different times and in different formats.

3) Disease Management: The modem (51) enables the smart medicine container (10) to communicate with other appropriately configured medical devices such as blood pressure monitor, glucose meter, coagulation meter and the like. The pill dispensing assembly is able to initiate, change or discontinue a medicine regimen based on information received from the medical devices. The microprocessor (71) is programmed with instructions on changes to be made based on information received from medical devices. These instructions can be fed either at the time of filling a prescription or remotely. Alternatively, data obtained from medical devices can be sent to a health care professional who can then remotely change a medicine regimen. It is evident from the foregoing discussion that the smart medicine container (10) can play an important role in comprehensive disease management and improve clinical outcomes. This unique feature of the present invention also reduces the need for a patient to go to physician's office.

4) Epidemic Control: A multitude of smart medicine containers (10) are connected to a central server to form a network. The central server can access medicine regimen data of all smart medicine containers (10) within the network. The server can remotely send a command to all smart medicine containers (10) containing an effective medicine, instructing the pill dispensing assembly therein to dispense prescribed doses and alert the patient. In addition, the central server can send information about the epidemic to all smart medicine containers (10) within the network. This information is displayed on the electronic display unit (25) or played in audio using the speakers (27). It is to be appreciated from the foregoing discussion that the smart medicine container (10) can be a powerful tool in controlling an epidemic by 1) instantly dispensing effective medicines to a large number of at risk patients and 2) quickly disseminating information about the epidemic, including preventive measures, to a large number of people.

5) Medicine Recall: Medicines are sometimes recalled from the market based on newly discovered adverse effects. The central server instructs all smart medicine containers within the network containing the recalled medicament to immediately stop dispensing the said medicament. The central server also instructs the smart medicine containers to display the recall information on their electronic display units. It is evident from the above discussion that the smart medicine container enables a quick and extremely cost effective method to withdraw a medicine from the market.

6) Web Based Medicine Inventory Management System: This provides a dynamic inventory status of the smart medicine containers within the network and can be helpful in inventory management and product tracking. A pharmacy can review the inventory of all smart medication containers within its network and quickly assess the demand for various medicines based on the remaining refills. It can then accordingly stock its inventory and update its supply chain.

7) Web Based Compliance Monitoring System: The server stores compliance data from all smart medicine containers in its network. This data is made accessible to authorized parties like physicians. In addition, an interactive web site and intelligent application software capable of data analysis can provide a comprehensive solution in dose administration of non complaint patients. This data can also be helpful to researchers in studying, among other things, epidemiology of diseases and patient behavior patterns.

Pill bridging is a major problem with any pill dispensing assembly. The present invention has multiple unique features that prevent pill bridging. The first layer of protection is provided by the 'U' or 'V' shaped storage compartment (11) with a regulating wheel (15) with pill receptacles (24) guarding its outlet. This assembly enables an orderly and controlled discharge of pills (121) from the storage compartment onto the collecting conveyor belt (16). The use of gravitational force to discharge pills (121) from the pill receptacles of the regulating wheel onto the collecting conveyor belt (16) provides the second layer of protection against pill bridging. Even if multiple pills (121) are present in the receptacle, each is discharged at a different instance, thus providing pill separation. The collecting conveyor belt (16) moves at a faster speed than the rotational speed of the regulating wheel (15) which provides the third layer of protection against pill bridging. It amplifies the pill separation provided during discharge of pills (121) from the regulating wheel (15). The pills (121) are then discharged onto the dispensing conveyor belt (17). The separation of pills (121) at this stage is further amplified by moving the dispensing conveyor belt (17) at a faster speed than the collecting conveyor belt (16). This provides the fourth layer of protection against pill bridging. We believe that these four layers of protection provide a very reliable mechanism to prevent pill bridging and allow for an accurate dispensation of prescribed quantity of medicine.

Figure 12:
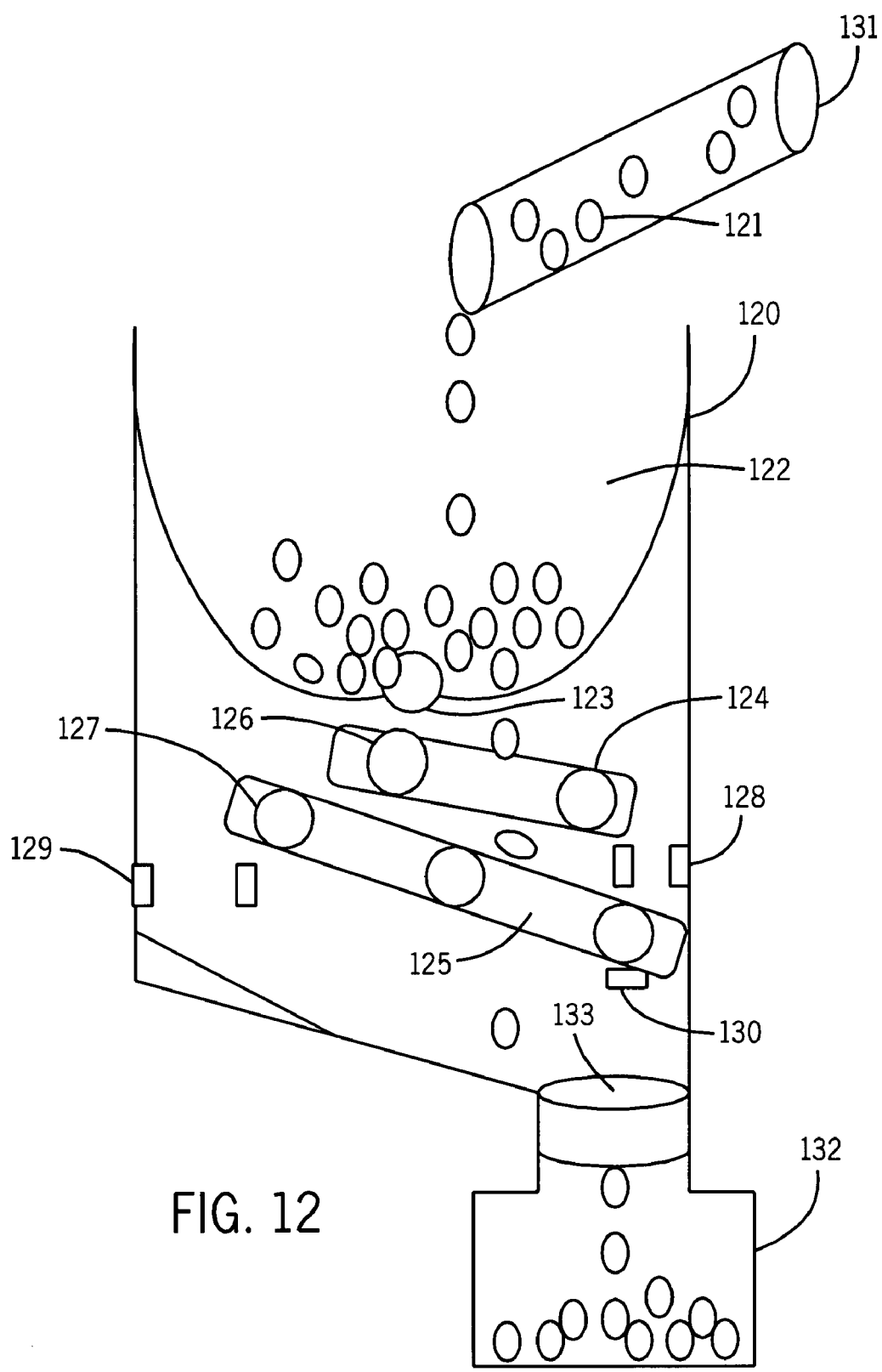
FIG. 12 shows the pill dispensing assembly of the present invention adapted for use in the pharmaceutical industry, such as to fill multiple pill bottles with a fixed quantity of pills.

According to another aspect of the present invention, the pill dispensing assembly can adapted for use in the pharmaceutical industry to dispense a desired quantity of medicine, such as to fill a prescription at the pharmacy or to fill multiple medicine bottles with a fixed number of pills. This aspect of the present invention is shown in FIG. 12. The pill dispensing assembly is placed in a housing (120) which has a storage tank (122) on top, dispensing assembly in the middle and an outlet bay at the bottom. Pills (121) are conveyed into the storage tank (122) using an appropriate mechanical assembly, which in the preferred embodiment is a tube (131). The outlet from the storage tank (122) into the dispensing assembly is guarded by a regulating wheel with two receptacles (123). The outlet door (133) at the bottom of the housing is coupled with a pill bottle (132). The dispensing assembly comprises of a collecting conveyor belt (124) and a dispensing conveyor belt (125) that move on two separate sets of wheels (126&127). Photoelectric sensors (128&129) are provided along the path of relay of pills between the collecting conveyor belt (124) and the dispensing conveyor belt (125) and between the dispensing conveyor belt (125) and the outlet bay. A photoelectric sensor (130) is also provided at the outlet door (133) which is activated when the pill bottle (132) is removed from the outlet door (133). A separate control unit housing a processor, memory chip and a plurality of control switches is provided (not shown).

Once the command to dispense pills is given, the dispensing conveyor belt (125) is activated. This ensures that any remaining pill on the dispensing conveyor belt (125) from previous cycle is dispensed before a fresh batch is released from the storage tank (122). The dispensing conveyor belt (125) stops if desired number of pills (121) is dispensed before completion of one cycle. If the desired number of pills (121) is not dispensed within the first cycle, the remainder of the pill dispensing assembly comprising of the regulating wheel (123) and collecting conveyor belt (124) is activated. The pill receptacles of the regulating wheel (123) collect pills (121) from the storage tank (122) and dispense them onto a moving collecting conveyor belt (124). The speed of the collecting conveyor belt (124) is greater than the rotational speed of the regulating wheel (123) which amplifies the pill separation provided by the regulating wheel (123). As the pills (121) fall from the collecting conveyor belt (124) onto the dispensing conveyor belt (125), they are counted by photoelectric sensors (128), which relay this data to the processor and memory chip. Once the processor senses that desired number of pills (121) have been dispensed, it stops the regulating wheel (123) and the collecting conveyor belt (124). The collecting conveyor (124) transfers the pills (121) onto a moving dispensing conveyor belt (125). The dispensing conveyor belt (125) moves at a greater speed than the collecting conveyor belt (124) which further amplifies the pill separation achieved so far. The dispensing conveyor belt (125) transfers the pills (121) into the outlet bay. The photoelectric sensors (129) count the pills (121) as they fall from the dispensing conveyor belt (125) into the outlet bay and relay this data to the processor and memory chip in the control unit. The dispensing conveyor belt (125) stops once the processor signals that desired quantity of pills (121) have been dispensed. In effect, the entire pill dispensing assembly of the smart medicine container is inactivated at this time. Alternatively, in situations where a fixed number of pills is to be dispensed in multiple pill bottles, the filled pill bottle (132) is replaced by an empty pill bottle at the outlet door (133). The removal of the pill bottle (132) from the outlet door (133) is captured by a photoelectric sensor (130), which relays this information to the processor which keeps a count of the number of pill bottles that have been removed. The replacement of pill bottles at the outlet door (133) can be done manually or can be done automatically using a conveyor assembly.

What is claimed is:

1. A dispenser for dispensing a predetermined number of dosages of a medicine from a bulk supply of the medicine, the dispenser having first and second opposite sides portions, comprising:
   a dispensing compartment;
   a storage container for receiving the bulk supply of the medicine therein, the storage container having a discharge port;
   a first conveyor having inlet and outlet ends and traveling at a first rate of speed in a first direction toward the first side portion of the dispenser, the first conveyor receiving at least one dosage of medicine thereon from the discharge port and transporting the at least one dosage to the outlet end;.
   a second conveyor having an inlet and outlet ends, the second conveyor traveling at a second rate of speed greater than the first rate of speed in a second direction toward the second side of the dispenser;
   wherein:
   the inlet end of the second conveyor receives the at least one dosage from the outlet end of the first conveyor and transports that at least one dosage to the dispensing compartment.

2. The dispenser of claim 1 further comprising of a first sensor positioned adjacent the outlet end of the second conveyor for counting the at least one dosage deposited in the dispensing compartment.

3. The dispenser of claim 2 further comprising a second sensor positioned adjacent the outlet end of the first conveyor for counting the at least one dosage received on the second conveyor from the outlet end of the first conveyor.

4. The dispenser of claim 2 further comprising:
   a drive system for driving the first and second conveyors; and
   a control system operatively connected to the first sensor and to the drive system for controlling the operation of the drive system;
   wherein the first sensor provides corresponding counting signals to the control system in response to at least one dosage counted and wherein the control system terminates operation of the drive mechanism in response to the number of dosages counted being equal to the predetermined number of dosages.

5. The dispenser of claim 4 wherein the control system includes a microprocessor and a memory device for storing predetermined information.

6. The dispenser of claim 4 further comprising a user interface operatively connected to the control system, the user interface allowing a user to transmit predetermined information to the control system.

7. The dispenser of claim 4 further comprising a communication link interconnecting the control system to a communication network, the communication link transmitting information to and receiving information from the communication network.

8. The dispenser of claim 7 wherein the control system is operatively responsive to the information transmitted on and received from the communication network.

9. The dispenser of claim 1 further comprising an outlet door movable between a first locked position preventing user access to the dispensing compartment and a second unlocked position allowing user access to the dispensing compartment.

10. The dispenser of claim 9 further comprising a memory storage device for storing predetermined information and wherein the movement of the outlet door from first locked position to the second unlocked position is recorded in the memory storage device.

11. The dispenser of claim 9 further comprising a locking mechanism operatively connected to the outlet door and being movable between a first unlocked position wherein the outlet door is movable between open and closed positions and a second locked position for maintaining the outlet door in the closed position.

12. The dispenser of claim 11 wherein the locking mechanism includes a radio frequency identification reader, the locking mechanism movable to the unlocked position in response to a predetermined radio frequency tag received by the reader.

13. The dispenser of claim 9 further comprising a cap for selectively isolating the storage compartment from an environment outside of the dispenser.

14. The dispenser of claim 1 wherein:
   the first conveyor extends along a first axis;
   the second conveyor extends along a second axis; and
   the first axis intersects the second axis at predetermined acute angle.

15. The dispenser of claim 1 wherein the first conveyor extends along a first axis, the first axis being at a predetermined acute angle to horizontal.

16. The dispenser of claim 1 wherein the second conveyor extends along an axis, the axis being at predetermine acute angle to horizontal.

17. A dispenser from dispensing a predetermined number of dosages of a medicine from a bulk supply of the medicine, comprising:
   a dispensing compartment;
   a storage container for receiving the bulk supply of the medicine therein, the storage container having a discharge port;
   a first conveyor at a predetermined acute angle to horizontal and having inlet and outlet ends, the first conveyor configured to receive at least one dosage of medicine thereon from the discharge port and to transport the at least one dosage to the outlet end;
   a second conveyor at a predetermined acute angle to horizontal, and having inlet and outlet ends, the second conveyor configured to receive the at least one dosage from the outlet end of the first conveyor and to transport the at least one dosage along an upwardly inclined path to the dispensing compartment;
   a first sensor positioned adjacent the outlet end of the first conveyor for counting the at least one dosage received on the second conveyor from the first conveyer;

a second sensor positioned adjacent the outlet end of the second conveyor for counting the at least one dosage deposited in the dispensing compartment; and a drive mechanism operatively connected to the first and second conveyors for driving the conveyors at corresponding speeds.

18. The dispenser of claim 17 further comprising a control system operatively connected to the drive mechanism and to the first and second sensors, the control system actuating the drive mechanism in response a predetermined parameter.

19. The dispenser of claim 18 further comprising a user interface operatively connected to the control system, the user interface allowing a user to transmit predetermined information to the control system.

20. The dispenser of claim 18 further comprising a communication link interconnecting the control system to a communication network, the communication link transmitting information on and receiving information from the communication network.

21. The dispenser of claim 18 wherein the first and second sensors provide corresponding counting signals to the control system in response to the at least one dosage counted and wherein the control system terminates operation of the drive mechanism in response to the number of dosages counted being equal to the predetermined number of dosages.

22. A method of dispensing a predetermined number of dosages of a medicine from a bulk supply of the medicine, comprising the steps of:

transporting one of the dosages of the medicine with a first conveyor, the first conveyor traveling at a first speed in a first direction towards a first side portion of a dispenser;

depositing the one of the dosages of the medicine on a second conveyor positioned below the first conveyor, the second conveyor traveling along an upwardly inclined path at a second speed in a second direction toward a second side portion on the dispenser; and depositing the one of the dosages in a dispensing compartment of the dispenser.

23. The method of claim 22 wherein the second conveyor moves at a speed greater than the first conveyor.

24. The method of claim 22 comprising the additional step of repeating the step of transporting one of the dosages until the counted dosages equals the predetermined number of dosages.

25. The method of claim 22 comprising the additional step of providing a user to access the dispensing compartment after the number of counted dosages equals the predetermined number of dosages.

26. The method of claim 22 comprising of the additional step of transferring the dosage of medicine dispensed in the dispensing compartment into another container.

* * * * *